(12) United States Patent
DeCurtis et al.

(10) Patent No.: US 10,911,893 B1
(45) Date of Patent: Feb. 2, 2021

(54) CONTACT TRACING VIA LOCATION SERVICE

(71) Applicant: DeCurits LLC, Orlando, FL (US)

(72) Inventors: David DeCurtis, Windermere, FL (US); Derek Fournier, Valrico, FL (US); Matthew Winans, Virginia Beach, VA (US); Debashis Choudhury, Dallas, TX (US); James Learish, Cary, NC (US)

(73) Assignee: DeCurtis LLC, Orlando, FL (US)

( * ) Notice: Subject to any disclaimer, the term of this patent is extended or adjusted under 35 U.S.C. 154(b) by 0 days.

(21) Appl. No.: 16/915,417

(22) Filed: Jun. 29, 2020

(51) Int. Cl.
*H04W 4/021* (2018.01)
*H04W 4/029* (2018.01)
*H04W 4/02* (2018.01)
*H04W 4/33* (2018.01)
*G11B 27/031* (2006.01)
*G06Q 10/06* (2012.01)
*G06K 9/00* (2006.01)
*A61B 5/024* (2006.01)
*H04L 29/06* (2006.01)

(52) U.S. Cl.
CPC ......... *H04W 4/023* (2013.01); *A61B 5/02427* (2013.01); *G06K 9/00771* (2013.01); *G06Q 10/06311* (2013.01); *G11B 27/031* (2013.01); *H04L 63/101* (2013.01); *H04W 4/021* (2013.01); *H04W 4/029* (2018.02); *H04W 4/33* (2018.02)

(58) Field of Classification Search
CPC ....... H04W 4/33; H04W 4/029; H04W 4/021; H04W 4/023; G06K 9/00771; G06Q 10/06311; H04L 63/101
See application file for complete search history.

(56) References Cited

U.S. PATENT DOCUMENTS

| 5,742,237 | A | * | 4/1998 | Bledsoe ................ G06Q 10/06 340/8.1 |
|---|---|---|---|---|
| 8,049,614 | B2 | | 11/2011 | Kahn et al. |
| 8,798,593 | B2 | | 8/2014 | Haney |
| 8,849,205 | B2 | | 9/2014 | Desai et al. |
| 8,862,067 | B2 | | 10/2014 | Un et al. |
| 9,357,342 | B2 | | 5/2016 | Viswanadham et al. |
| 9,418,531 | B2 | | 8/2016 | Basalamah et al. |
| 9,485,603 | B2 | | 11/2016 | Worrall et al. |
| 9,774,985 | B2 | | 9/2017 | Weizman et al. |
| 9,875,588 | B2 | | 1/2018 | McCollum et al. |
| 10,037,642 | B2 | | 7/2018 | Padgett et al. |

(Continued)

FOREIGN PATENT DOCUMENTS

EP        3046342 A1     7/2016

*Primary Examiner* — Julio R Perez (57) ABSTRACT

Systems, methods, and computer-executable instructions for contact tracing including receiving a first beacon identifier associated with a first person and a second beacon identifier associated with a second person over a time period from a plurality of readers. A location of the first person and the second person is determined. Health data associated with the first person is received. The first person is determined to be sick and a sick period of time is determined. Two or more people, including the second person, are determined to have been within a proximity of the first person during the sick period of time. A list of the two or more people is generated.

20 Claims, 6 Drawing Sheets

(56) References Cited

U.S. PATENT DOCUMENTS

| | | |
|---|---|---|
| 10,045,184 B2 | 8/2018 | Padgett et al. |
| 10,049,516 B2 | 8/2018 | Padgett et al. |
| 10,140,649 B2 | 11/2018 | Drake et al. |
| 10,157,514 B2 | 12/2018 | Padgett et al. |
| 10,171,978 B2 | 1/2019 | Padgett et al. |
| 10,238,976 B2 | 3/2019 | Ackley et al. |
| 10,304,271 B2 | 5/2019 | Padgett et al. |
| 10,499,228 B2 | 12/2019 | Padgett et al. |
| 2014/0122148 A1 | 5/2014 | Padgett et al. |
| 2015/0154844 A1* | 6/2015 | Skaaksrud .............. B65B 25/02 340/539.13 |
| 2016/0026837 A1* | 1/2016 | Good ..................... G16H 40/20 340/539.13 |
| 2016/0183042 A1 | 6/2016 | Weizman et al. |
| 2016/0217496 A1 | 7/2016 | Tuchman et al. |
| 2016/0373893 A1 | 12/2016 | Khanna et al. |
| 2017/0209102 A1* | 7/2017 | Parthasarathy .......... A61B 5/01 |
| 2018/0276434 A1 | 1/2018 | Li et al. |
| 2020/0059774 A1 | 2/2020 | Padgett et al. |
| 2020/0279339 A1* | 9/2020 | Akutagawa ............ G06Q 50/12 |

* cited by examiner

CONTACT TRACING VIA LOCATION SERVICE

BACKGROUND

Location services use beacon readers to read beacon information transmitted from beacons. An individual beacon reader is able to determine a distance to the beacon, but is unable to determine the beacon's specific location. Location services collect data from multiple beacon readers, each detecting the same beacon, to determine the beacon's location.

Contact tracing involves identifying individuals that may have been exposed to an infection. People that have been in close contact with someone known to be infected are identified. These individuals may self-quarantine to reduce the spread of the infection. As people may travel using public transportation or come into contact with a number of unknown individuals, there is a need to identify and communicate with people that have been possibly exposed to an infected individual.

DETAILED DESCRIPTION

Beacon information transmitted from beacons is relatively lightweight. For example, a 30 byte packet, e.g., beacon information, may be transmitted from a beacon. This packet may be transmitted multiple times each second. As an example, some protocols have the beacon information transmitted ten times each second. In a proximity based location system, multiple beacon readers detect a transmission from a beacon. The beacon information from each of detected readers may be transmitted to a location service that uses the beacon information and the location of the readers that detected the beacon information to calculate a location of the detected beacon.

A location service or location system is able to determine the location of a large number of beacons. A beacon may be worn by a person or attached to an object. Using the determined location of beacons, the location service, or another service that uses the data from the location service, is able to determine where beacons were over a period of time. Accordingly, a path of a beacon through an area may be determined. In addition, when the beacon was at a particular point on the path is also able to be determined from the data from the readers. Using the paths and times traveled of multiple beacons, which beacons have come into proximity with one another may be determined. In addition, the amount of time that the beacons where in proximity to one another may be determined. For example, two beacons may be determined to have been within proximity of one another for twenty minutes. Accordingly, the location service may be used to contact trace an infection through a population. With the threat of infections being able to rapidly spread through an area, there is a need for enhanced contact tracing. In addition, using a location service allows more efficient and accurate data analysis, compared to relying on self reporting.

In addition, information from a kiosk may be used to supplement data from the location service. For example, the kiosk may include the ability to read an individual's temperature. The kiosk may also include facial recognition to determine the individual or may be a beacon reader that reads a beacon associated with the individual. If the kiosk determines an individual is sick, the individual may be denied entrance to an area. For example, an individual may be denied boarding a ship and directed to an infirmary. The location service may also integrate cameras to read health data of individuals. Health data may include body temperature, heart rate, oxygen levels, etc. Health data determined by the location service may also be supplemented with health data from other devices, such as personal health devices. Combining the collection and analysis of health data combined with time and location data, allows for automatic detection of sick individuals combined with contact tracing of that individual through an area.

Figure 1:
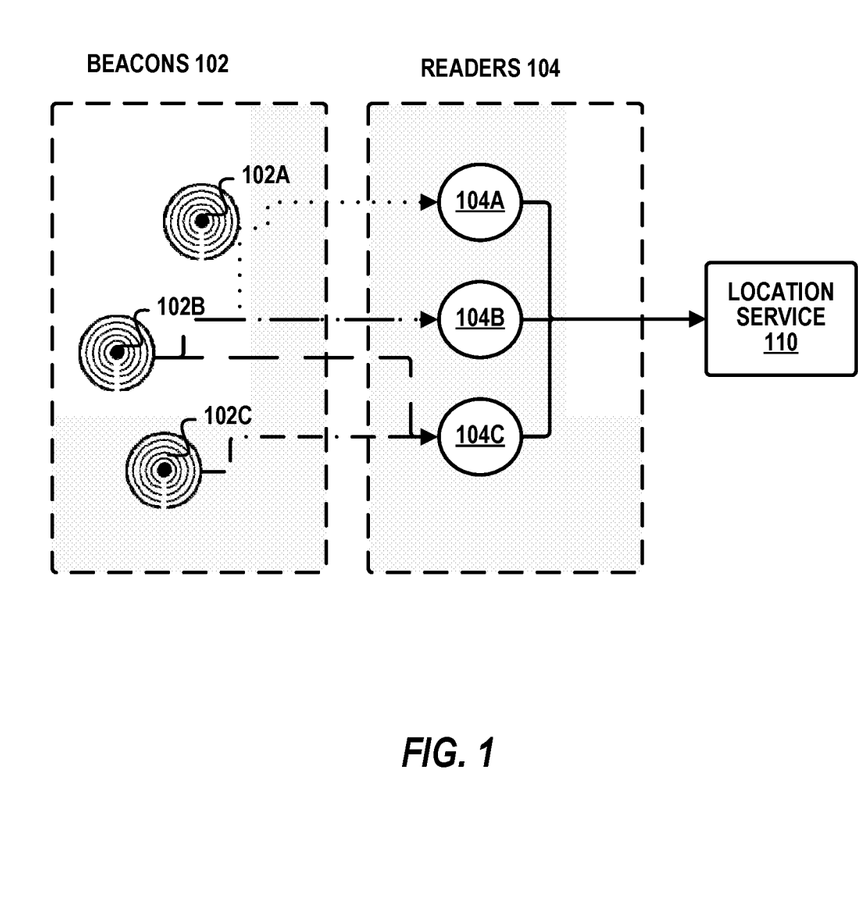
FIG. 1 is a system diagram of a location service system in accordance with respective examples.

FIG. 1 is a system diagram of a location service system in accordance with respective examples. The location service 110 may be used to determine when and where beacons 102 where located within an area. The system includes beacons 102 and beacon readers 104 that are part of a proximity system that provides proximity information to a location service 110. Beacons 102A, 102B, 102C may be carried by individuals or attached to objects such as luggage, equipment, etc. The beacons 102A, 102B, 102C advertise their presences by broadcasting beacon information to readers 104A, 104B, 104C. In an example, the readers 104A, 104B, 104C, detect beacons using Bluetooth Low Energy (BLE). The beacon information may be continuously broadcast from the beacons 102A, 102B, 102C. The beacon information may include a beacon identifier and a transmission strength. The readers 104A, 104B, 104C detect the beacon information from one or more of the beacons 102A, 102B, 102C. Individually, the readers 102A, 102B, 102C are able to determine a distance between the reader and the detected beacon. The reader, however, is not able to determine a position of the beacon. Accordingly, the reader is able to detect advertised beacon information from beacons that are in the proximity of the readers.

Beacon information, or a portion of beacon information, along with potentially the proximate distance between a reader and a beacon may be sent to a location service 110. The location service 110 is able to use beacon information related to the same beacon, e.g., 102B, from multiple readers, e.g., 104B and 104C, to calculate a position or location of the beacon. For example, the location service 110 may use triangulation based on beacon information from three or more different readers. The location service 110, therefore, is able to determine a position of the beacon 102A. The position may be used to derive additional location information. In various examples, the location service 110 may provide location information to an application (not shown). The location service 110 may include a location engine that may be used to determine a position of a detected beacon.

The location service 110 may be connected to the readers 104 via a network. The network has a limited data bandwidth based on various factors known in network design. The readers 104 may receive beacon information multiple times a second, e.g., 5 times, 10 times, 15 times, from each detected beacon. In addition, multiple beacons may detect the same advertised beacon information from a single beacon. Prior art systems have transmitted every detected beacon information from every reader to a location service. Such a solution may tax the available network bandwidth. In some instances, the network bandwidth has become saturated with data from the readers. Redundant networks may be used to increase the available bandwidth, but comes with the cost of supporting and installing a second network. In some examples, the location services may be installed on a cruise ship or within an existing building, such as a hotel, hospital, etc., such that adding a second network may be cost prohibitive or physically impossible. In addition, given errors in accuracy in the distance determination results in the location service receiving low quality data. Combined with receiving all detected beacons, the errors in accuracy results in the location service receiving a large volume of low quality data.

The readers 104 may implement various disclosed features to reduce data traffic flow. For example, the readers may detect beacons over a read delay period. The read delay period may be greater in length than the beacon information advertising rate, such that a beacon reader may receive multiple beacon information from a single beacon during the read delay period. As a specific example, beacon information may be transmitted ten times each second. The read delay period may be set to 0.5 seconds, 1 second, 5 seconds, etc. During the read delay period, the readers 104 detect advertised beacon information from the beacons 102. At the end of the read delay period, each reader 104 may transmit to the location service 110 a single detect indication for each detected beacon. This feature may result in a 10× to 30× reduction in data traffic.

The data provided to the location service 110 from the readers 104 may include a beacon identifier that identifies the detected beacon 102. In addition, a calculated distance between the reader 104 and the beacon 102 may also be included in the data provided to the location service 110. The calculated distance may be based on an average distance of the detected beacon during the read delay period. In another example, the distance may be the last detected distance. In yet another example, the distance may be an average distance of a last number of detections. For example, the last 50% of detected beacon information may be used to calculate the average distance, while ignoring the first 50% of detected beacon information in the average distance calculation.

The average distance calculation may also be used to determine if a beacon has moved more than a distance threshold since the last read delay period. If a beacon has not moved more than this distance threshold since the last read delay period, the beacon reader may choose not to provide an indication that the beacon was detected. In this example, the location service may determine the location of the beacon to be the last reported distance of the beacon. As an example, the distance threshold may be 1 meter; 3 meters; 5 meters; etc. The distance threshold may be based on a percentage of the previously reported distance. For example, the distance threshold may be 10%, 20%, 35%, etc., of the previously reported distance. In addition, the distance threshold may be set based on the features of the beacon reader. For example, a beacon reader may be able to determine an angle of approach or angle of departure of a beacon. These angles may allow the beacon reader to calculate a more accurate beacon distance, i.e., the distance between a beacon and a beacon reader that detects the beacon. The availability of a more accurate beacon distance may be used to reduce the distance threshold used.

The distance threshold may be used to help ensure a better quality of information is provided to the location service. For example, the accuracy of the beacon distance calculation may decrease as the distance between the beacon and the beacon reader increases. Accordingly, the distance threshold may be determined based on the average distance. If the beacon is determined to be close to the beacon reader, e.g, within 3 meters, the distance threshold may be set to a smaller value compared to when the beacon is determined to be further away, e.g, more 7 meters. This ensures that the beacon reader takes into account the accuracy of the distance calculation. Reporting to the location service when the beacon reader detects actual movement of the beacon means the location service is getting higher quality data compared to receiving all of the data from the beacon reader.

Another feature that may be used to reduce data traffic is the use of a read radius. Some known beacon reader technology loses accuracy as the beacon is farther away from the reader. For example, a distance calculation of a beacon that is within 5 meters of the reader may have an accuracy of +/−0.25 meters. Beacons that are detected to be 5-10 meters from the reader may have an accuracy of +/−3 meters. In some examples, beacons that are detected by a reader but are determined to be further away than a read radius from the reader may be ignored. Ignoring a detected beacon may mean that the reader ignores the detected beacon information in any average distance calculation. Another example is when the calculated average distance is greater than the read radius. In this example, ignoring the detected beacon means not sending an indication to the location service regarding the beacon when the calculated average distance is greater than the read radius.

Figure 2:
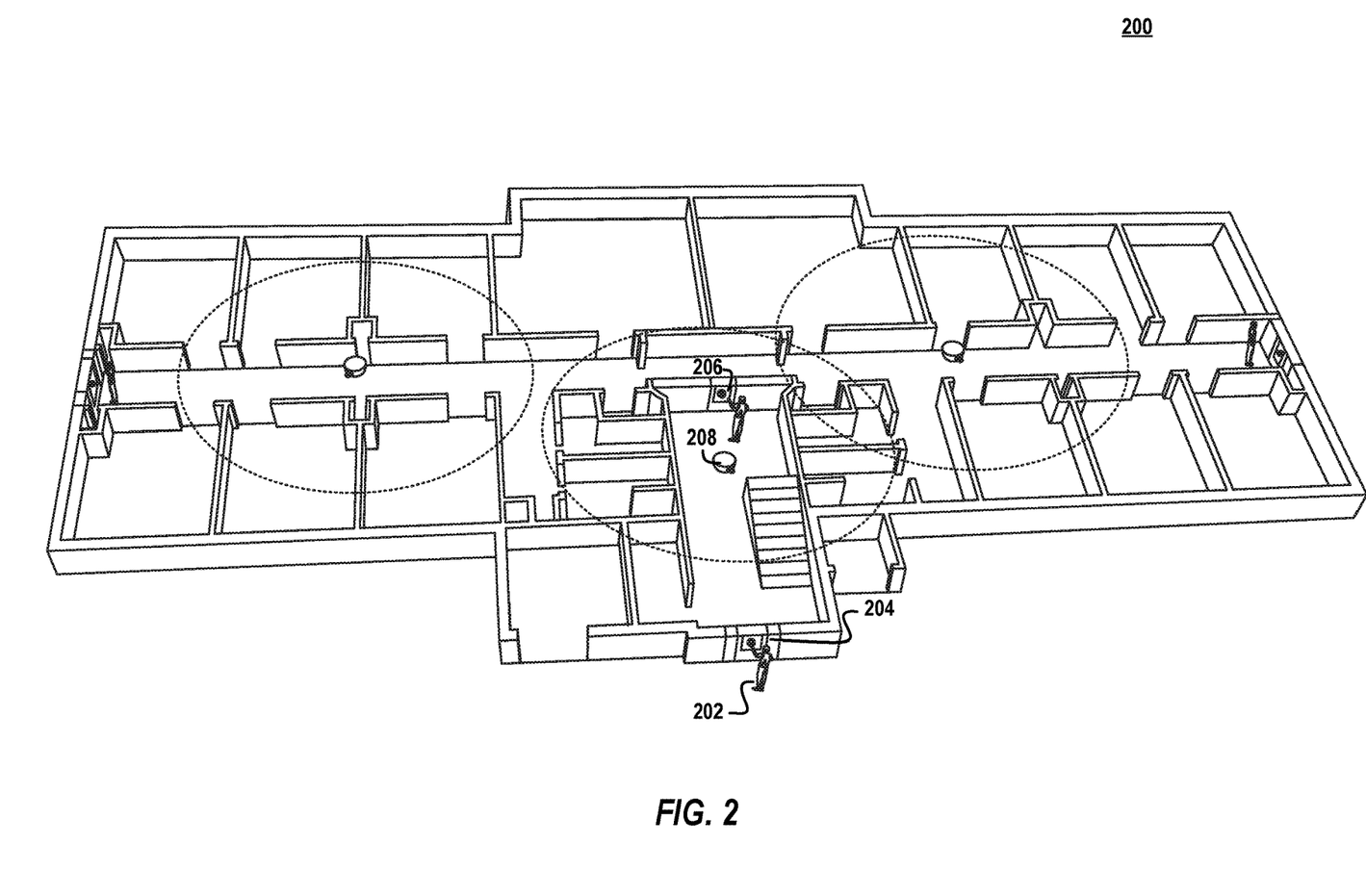
FIG. 2 is a diagram illustrating an area with location based contact tracing in accordance with respective examples.

FIG. 2 is a diagram illustrating an area 200 with location based contact tracing in accordance with respective examples. An individual 202 may desire to enter the area 200. The area 200 may be a building, such as a hospital, hotel, school, etc. As another example, the area 200 may be a cruise ship. A kiosk 204 may be placed at an entrance of the area 200 or near an entrance to the area 200. For example, the kiosk 204 may be located on a gangway that leads to a cruise ship. The kiosk 204 may include a camera, user interface, and health sensors. The camera may be used to capture video of the individual 202. The video may then be used to recognize the individual 202 using facial recognition. The kiosk 204 may include a user interface that accepts input from the individual 202. For example, the individual 202 may enter their name or request access to the area 200. The kiosk 204 may also include health sensors that are used to collect health data from the individual 202. For example, the kiosk 204 may include a temperature sensor that captures the body temperature of the individual 202. The temperature sensor may be an infrared camera. The kiosk 204 may relay any information gathered by the kiosk 204 to a remote device (not shown).

Using the health information and information received from the individual 202, access to the area 200 may be determined. For example, if the individual 202 appears to be healthy, access may be granted to the individual 202. If the health data indicates that the individual 202 is sick, then access to the area 200 may be denied. Access to the area 200 may controlled by locking or unlocking an entrance to the area 200. In one example, if the individual 202 appears to be sick the kiosk 204 may indicate to the individual 202 or other personnel that the individual 202 is to report to an infirmary that may be located within the area 200.

The area 200 may include multiple kiosks, such as kiosk 206. Data from multiple kiosks may be collected and analyzed together to determine if the individual 202 is sick. The kiosks may be able to identify the individual 202 using facial recognition or from information provided by the individual 202. Identifying the individual 202 along with the time the individual 202 was near a kiosks allows for tracing a path the individual 202 took navigating the area 200. In addition, beacon readers 208 may also collect health data. The beacon readers may also provide proximity information that may be used to determine a location of the individual 202.

Figure 3:
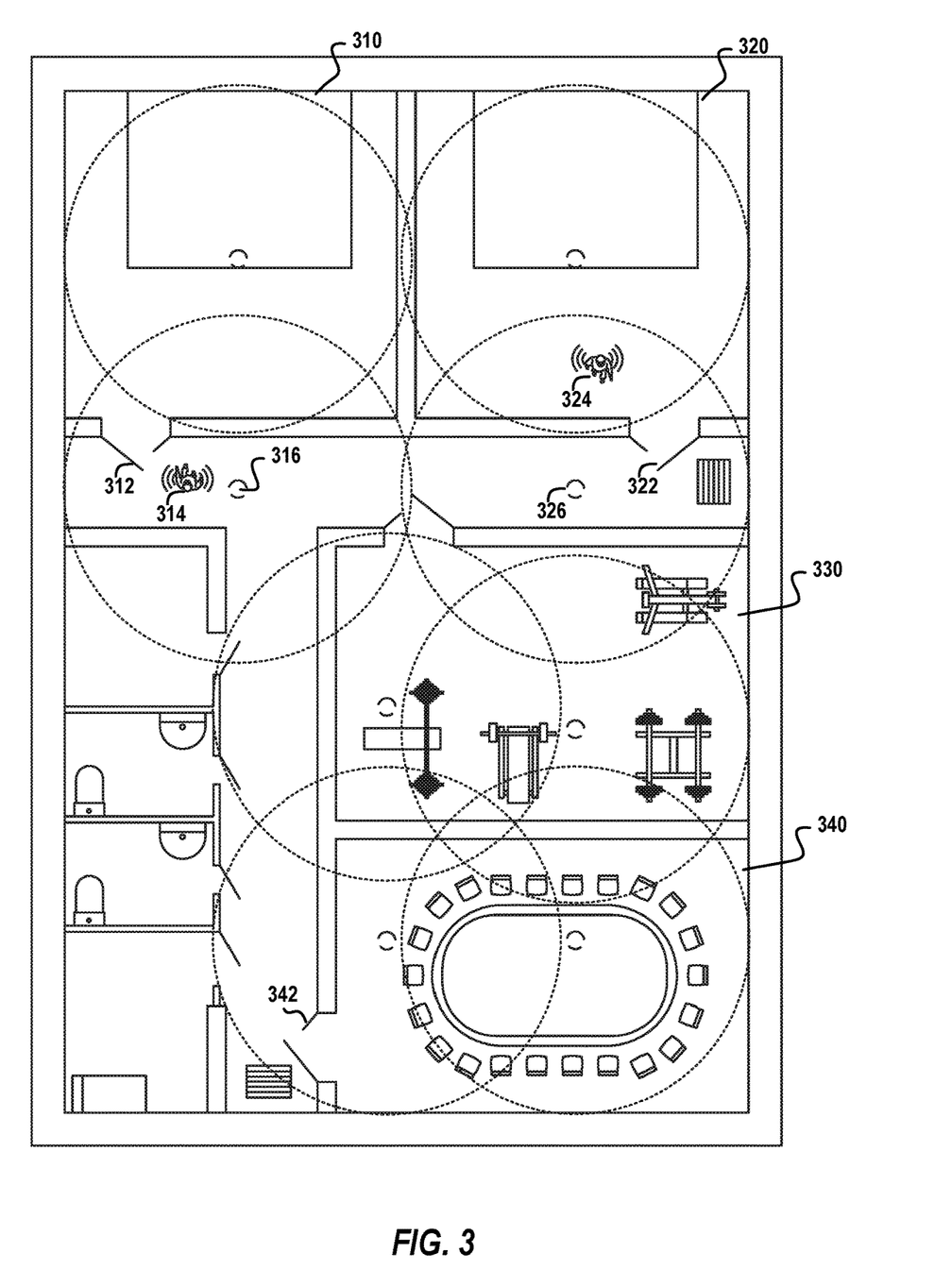
FIG. 3 is a diagram illustrating an area with location based contact tracing in accordance with respective examples.

FIG. 3 is a diagram illustrating an area 300 with location based contact tracing in accordance with respective examples. In this exemplary figure, the area 300 may be part of cruise ship or hotel. The area 300 includes rooms such as a gym 330, a casino 340, and two dining areas 310 and 320. Beacon readers, such as 316 and 326, may be installed within the area 300. The beacon readers detect beacons worn by individuals, such as 314 and 324. Data regarding detected beacons from multiple beacon readers may be combined to determine locations of the individuals 314 and 324.

Areas may have access controls that selectively unlock doors for particular individuals. For example, a door 342 to the casino 340 may be locked. As an individual approaches the door 342, a beacon associated with the individual may be detected by multiple beacon readers. One such beacon reader may be located near the door 342, such as within an access panel that displays information associated with the casino 342. The detected beacon may be used to determine if the individual has access rights to the casino. For example, someone under the age of 18 may be denied entry, such that the door 342 remains locked. If the individual, however, is over the age of 18, the door 342 may unlock granting the individual access to the casino. Other areas such as the gym 330 may allow access during certain times of the day.

Health data may be collected about individuals via health sensors integrated with the beacon readers, remote health sensors, or user-worn health sensors. As described in greater detail below, the health data may be used to determine if an individual is sick. The sickness determination may be used to modify the access list to areas. For example, an individual may be over the age of 18 and, therefore, may have access to the casino 340 and the gym 330. If the individual is determined to be sick the access list associated with the casino 340 and the gym 330 may be modified to exclude the sick individual. If the sick individual approached the casino 340, the door 342 would remain locked.

A sick individual, however, could still gain access to restricted areas. For example, a non-sick individual could be granted access to the casino 340. Once the door 342 opened, the sick individual could walk into the casino 340. Beacon readers located throughout the area 300 may be used to determine the location of sick individuals. If a sick individual is determined to be in a public place, an alert may be generated to the sick individual. The alert may instruct the individual to return to their room or report to an infirmary. An alert may also be generated for the crew or employees within the area. The alert may provide identifying information regarding the individual such that the crew may help escort the individual to a safe area.

The area 300 may also be configured to have designated areas for sick and non-sick guests. For example, the dining area 310 may be available for any sick guest, while the dining area 320 may be reserved for non-sick guests. Doors 312 and 322 may be in a locked state. An individual 314 has been determined to be sick based on health data associated with the individual 314. As the individual 314 approaches the door 312, the beacon reader 316 and other beacon readers not shown, detect a beacon associated with the individual 314. The door 312 or another device associated with door, such as an access panel, detects that the individual 314 is approaching. The door 312 or other device may then determine if the door 312 should be unlocked for the individual 314. As the dining area 310 is designated for sick individuals, the door 312 would unlock for the individual 314. The access list associated with the door 312 may be updated to include the individual 314 once the individual 314 is determined to be sick. Once the individual 314 is determined to no longer be sick, the access list associated with the door 312 is updated to remove individual 314. Accordingly, once the individual 314 has recovered, the individual 314 would not be granted access to the dining area 310.

Dining area 320 is similar to the dining area 310 in that access to the dining area 320 is controlled via a locked door 322. The dining area 320, however, is designated for non-sick individuals. Accordingly, the door 322 would not unlock if the sick individual 314 approached. A non-sick individual 324 has been granted access to the dining area 320. For example, when the individual 324 approached the door 322, the access list associated with the door 322 would be used to determine to permit access to the individual 324.

Figure 4:
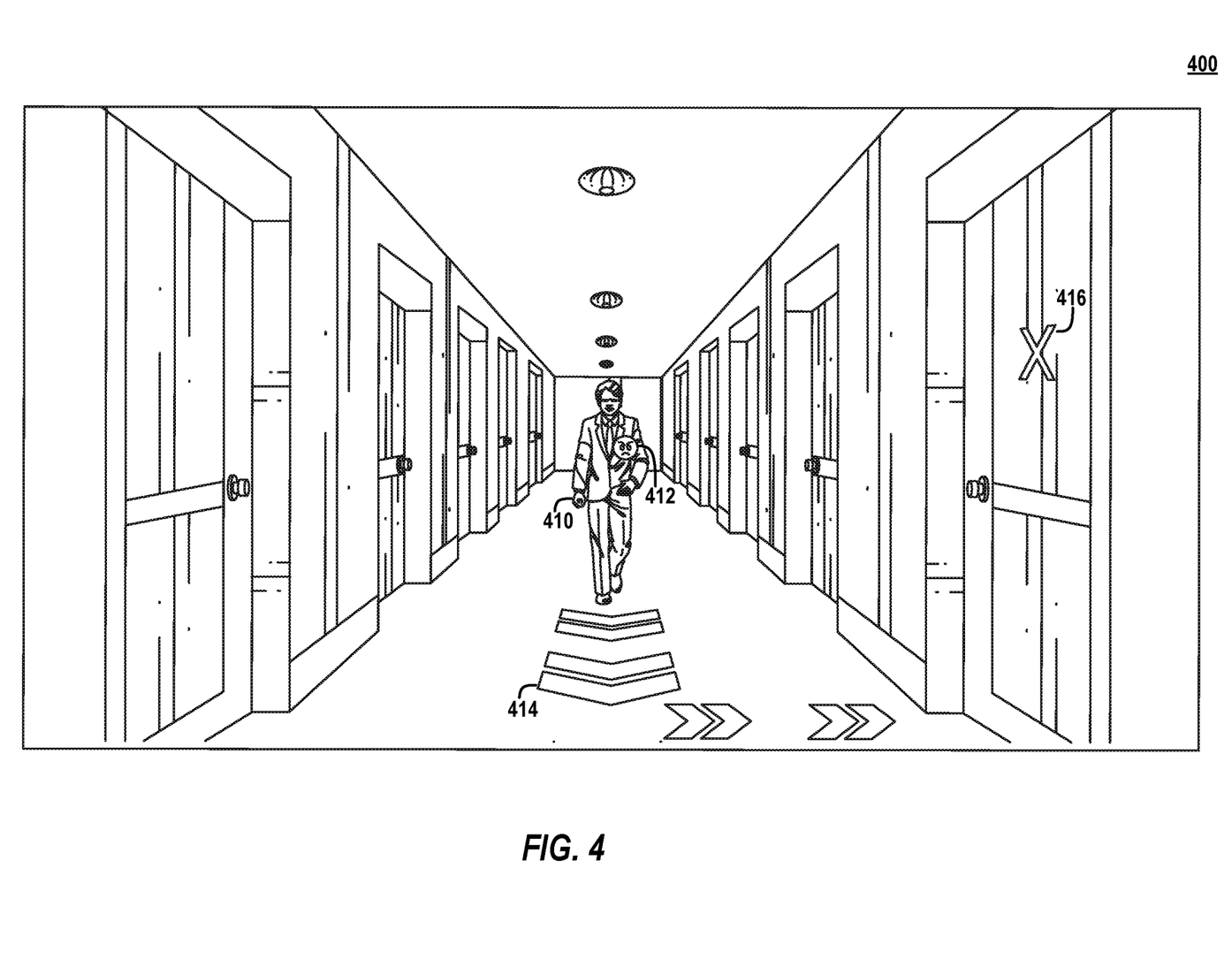
FIG. 4 is a diagram illustrating an augmented reality view in accordance with respective examples.

FIG. 4 is a diagram illustrating an augmented reality view 400 in accordance with respective examples. The augmented reality view 400 may be seen by an individual 410. The individual 410 shown has previously been determined to be sick. Path markers 414 may be used to show the individual 410 the route they should use to go back to their room or to another location, such as a quarantined area or infirmary. A crew member or other guests may also see portions or all of the augmented reality view. For example, other guests may see a sick indicator 412 on the guest. A crew member, such as a cleaning crew member, may see the path markers 414 to the guest room that requires disinfecting. In addition, a room indicator 416 may be seen to indicate that the room is associated with sick individuals. Again, crew members may see this indication 416 and know that the room requires cleaning. The augmented reality view 400 provides information for individuals to reduce or minimize the spread of an infection. For example, the sick individual may take the shortest and quickest path to a safe location. Other guests may see the sick individual 410 and stay the recommended distance away from the individual 410. Crew members or employees may use the augmented reality view to disinfect areas. For example, the path makers 414 may indicate the path a sick individual had taken through the entire area. A cleaning crew member may follow the path, thereby, disinfecting every area visited by the sick individual. In addition, the augmented reality view 400 allows crew and employees to quickly identify potentially sick individuals in public places. Appropriate action may then be taken by the crew or employee for the safety of the individual, other guests, the crew, and the general public.

Figure 5:
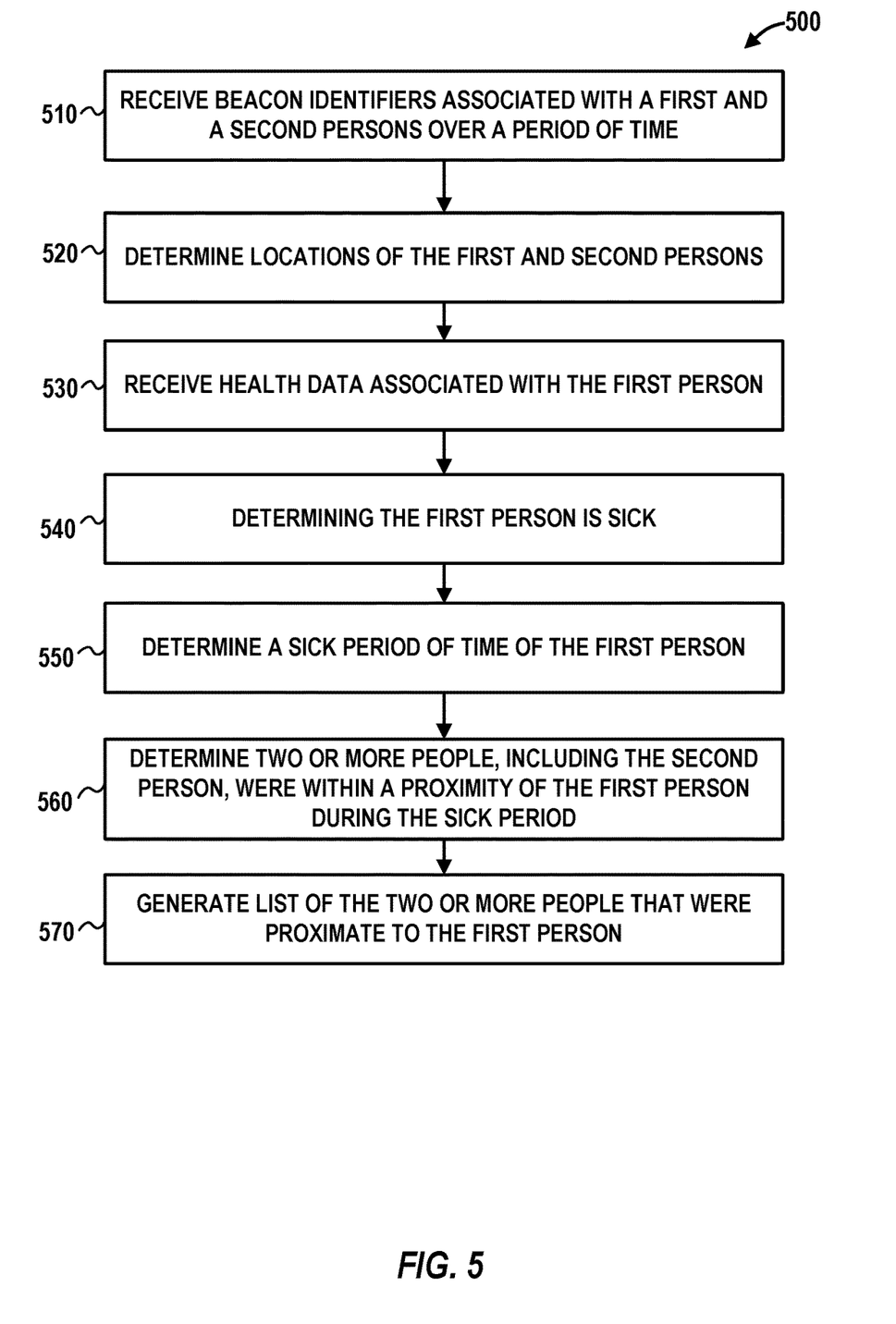
FIG. 5 is a diagram illustrating a flow diagram of a process for contact tracing in accordance with respective examples.

FIG. 5 is a diagram illustrating a flow diagram of a process 500 for contact tracing in accordance with respective examples. The process 500 may be executed on a computing device. The process 500 may be used by a location service to detect sick individuals and contact tracing of those individuals.

At 510, beacon identifiers associated with a first and a second person are received over a period of time. For example, a first person may be associated with a beacon identifier. This beacon identifier may be broadcast from a device that is worn or carried by the individual. Similarly, a second person may carry or wear a device that transmits a second identifier that is associated with the second person. These beacon identifiers may be transmitted continuously from the respective devices. Beacon readers, which are part of a location service, receive the beacon identifiers and provides them to a location service.

At 520, the locations of the first and second persons are determined from the received beacon identifiers. For example, the location service may aggregate data from different beacon readers to determine a location of a beacon. Accordingly, the data received from beacon readers may be used to determine the locations of a beacon over a period of time. In addition to location, the location service may also associate a time that indicates when the beacon was detected. The time may then be associated with when the beacon was at a particular location. Beacons from a number of guests, crew, employees, etc., may be received by the location service. The location service may determine the locations of each of these people in addition to the locations of the first and second persons.

At 530, health data associated with the first person is received. The health data may include one or more of a body temperature, heart rate, or oxygen level of a person. In some examples, the health data is received from a camera installed within the area covered by the location service. For example, a camera, such as an infrared camera, may be used to determine a body temperature of a person. Health data may also be received using a microphone, health sensors, or from a user device. For example, audio data from a location associated with a person may be received. The audio data may be used to generate health data associated with the person. For example, the audio data may be analyzed to determine if the person is coughing, vomiting, wheezing, gasping, etc. As another example, sensors within a location associated with a person may be used to generate health data. For example, a water meter or a sensor that detects the number of times a toilet is flushed may be used to generate the health data. In another example, an air sensor may be used to detect the presence of airborne pathogens may be used. The location associated with the person may be a room assigned to the person. In another example, health data may be received by a medical professional, such as a doctor or nurse. The health data may be temperature, heart rate, oxygen levels, medications, vital signs, etc. In another example, the health data may be a sick indicator that does not include any additional health data.

The health data may be associated with a beacon identifier using a number of different techniques. As an example, facial recognition may be used to match the health data with a beacon identifier. Voice recognition may also be used. The location where the health data was collected may also be used. For example, health data gathered in a private area assigned to a person may be used to match the health data to the person. In another example, the health data may be provided along with the beacon identifier that is broadcast from the beacon. For example, the beacon may be worn by a person in an accessory. This accessory may also monitor the person's heart rate, temperate, oxygen levels, etc. This health information, therefore, could be broadcast along with the beacon identifier. In yet another example, the device collecting the health data can determine a distance between the device and the person. This distance may be used with the distance between a beacon reader and beacon determined by the location service to determine which beacon identifier the health data is associated. For example, an infrared camera may be installed on one or more beacon readers. The distance between the camera and the person and the distance between the detected beacon and beacon reader will be similar. If those distances are within a particular distance threshold, the health data can be associated with the beacon identifier. For example, when the distances are within 0.25 meters (m), 0.5 m, 1 m, etc., the health data may be associated with the beacon identifier.

At 540, the first person is determined to be sick. In some examples, the first person is determined to be sick based on the health data. For example, a first person may be determined to be sick when their temperature is above a predetermined threshold for more than a particular amount of time. The location of the person may be used to adjust the threshold. For example, the threshold may be increased based on an area. Gyms and saunas are example locations where the threshold may be increased. Swimming pools are an example location where the threshold may be decreased. Other health data may also be used to determine if a person is ill. Lower oxygen levels or changes in a person's heart rate may be used to determine the person is sick. The sickness determination is configurable. For example, a person may have sustained low-grade fever. The low-grade fever by itself may not qualify the person as being sick. Additional health data may be used to determine if the person is sick. For example, the heart rate, oxygen levels, coughing, etc., may be used to determine that the person is sick. As an example, a person with a low-grade fever combined with detected coughing may be identified as sick. While someone that has just a low-grade fever would be identified as healthy. A higher temperature fever, such as 103 degrees Fahrenheit, by itself may determine the person is sick without the use of other health data.

In another example, the first person is determined to be based upon health data received from a health professional. For example, a nurse or doctor may indicate that a particular person is sick. Health data indicating the first person is sick is received by the contact tracing system. A beacon identifier associated the first person is determined. The beacon identifier may be used by the location service to track the location of the first person.

At 550, a sick period of time for the first person is determined using the health data. The sick period of time is within the time period when the beacon identifiers are received. The sick period of time may indicate when the person first started exhibiting signs of sickness. In another example, the sick period of time may take into account an incubation period of illness. In yet another example, the sick period of time may be provided by a health professional.

At 560, two or more people are determined to have been within a proximity of the first person during the sick period of time based on information from the location service. The past location data of various people may be used to determine which people were proximate to the first person. As an example, the locations of the first person and the second person may be used to determine that the second person was within a proximity of the first person during the sick period of time. In an example, determining the second person was within the proximity of the first person during the time period includes determining the second person was within a predetermined distance from the first person. In addition, determining the second person was in proximity to the first person may take into account how long the second person was proximate to the first person. For example, determining the second person was near the first person may include determining the second person was within the predetermined distance from the first person for more than a predetermined period of time. The predetermined time period and distance may be configurable. In an example, the distance and time may be based on a type of sickness associated with the first person. For example, the predetermined distance may be six feet and the predetermined period of time may be 5 minutes. In an example, the period of time may be cumulative of different times when the persons were proximate to one another. For example, the first person and second person may be within six feet of one another for three minutes. Then at a later time, the first and second person may be within six of one another for another three minutes within the sick period. In total, the first and second person were near one another for more than five minutes. In some examples, this cumulative amount of time indicates that the first person and second person were proximate to one another.

At 570, a list of the two or more people that were proximate to the first person is generated. The list may be printed, emailed, or displayed to employees or health professionals. The list may be used to determine individuals that should be alerted regarding being proximate to the first person. For example, an employee may use the location service to identify In some examples, an alert associated with the second person may be generated based on the determination that the first person is sick. The alert may be provided to the second person and indicate that the second person was recently in the proximity of a sick person. The second person may self quarantine based on this alert. In addition to an alert, other actions may be taken based determining the first person is sick. For example, the first person may be removed from access rights to a location. As an example, the first person may be allowed in a public area, such as a restaurant. Once the first person is identified as sick, the first person may be removed from the access list to the restaurant. The first person, however, may be added to an access list for a different location. For example, a restaurant that caters to sick individuals may have the first person added to the corresponding access list. In addition, a list of all individuals that were proximate to the first person during the sick period of time may be generated.

Once a person is determined to be sick, the location service may generate a path through the area indicating where the sick person had been. The location service may also determine possible infected locations where the sick person visited during the sick period of time. A list of individuals that were within a possibly infected location may be determined. The amount of time a person spends in a possibly infected location may be used to determine if the person is at risk of being infected. An alert based on this risk may be provided to the person.

The path and/or the locations may be used to generate a cleaning schedule. The cleaning schedule may include each of the infected locations to be cleaned. In an example, a cleaning employee may use augmented reality to see the path taken be a sick person. In this example, video of an area is altered to show the path taken by the sick person through the area. The cleaning employee may use this path to effectively clean and neutralize surface contagions. The video may also be altered to show that one or more of the infected locations is currently closed to guests. In another example, the video may be altered to provide an indication if a sick person is within the area. For example, if the first person is walking down a hallway, video of the first person may be altered by placing a sick indicator over the first person or on the first person.

One or more of the infected locations may be a public area that is temporarily closed. In this example, access rights to the closed locations may be changed. For example, a casino may be closed. Normally, any guest of a hotel or a cruise ship may be able to access the casino. Doors going to the casino may automatically unlock to allow guests access to the casino. In an example, the casino doors may unlock based on a beacon identifier being detected in the vicinity of the casino doors. Normally, the casino doors may not unlock for guest that are below a specific age. If the casino has been temporality closed due to a sick person spending more than a predetermined amount of time in the casino, the access list associated with the casino doors may be changed to not admit any guest into the casino. Once the casino has been cleaned and determined safe, the access list may be updated to allow guests to once again enter the casino. An indication that a location has been disinfected may be sent from cleaning employees to a device.

In a specific example, beacon readers may be installed throughout a cruise ship. Guests and crew of the cruise ship may wear a beacon. As guests and crew move through the cruise ship, the beacon readers may detect the worn beacons. A location service may collect data from multiple beacon readers to determine when a guest or crew was at a particular location. In addition, data from cameras, such as closed circuit cameras, may be used to recognize guests and crews. The location data from the location service and the recognition data from camera may be combined to construct a path that a guest took through the cruise ship. In addition to the path, the time when a guest was a point on the path may also be determined. Constructing the path and time data from multiple guests allows for the determination of what guests and crew were near other guests and crew. If someone is determined to be sick, a list of individuals that were in close proximity to the sick individual may be determined. In addition, the locations and the time spent at those locations by the sick individual may be determined. When a cruise ship is preparing to dock at a location, list of sick individuals and those individuals that were close proximity to a sick individual may be generated. This list may be used to quarantine individuals and allow/prevent boarding of individuals.

Figure 6:
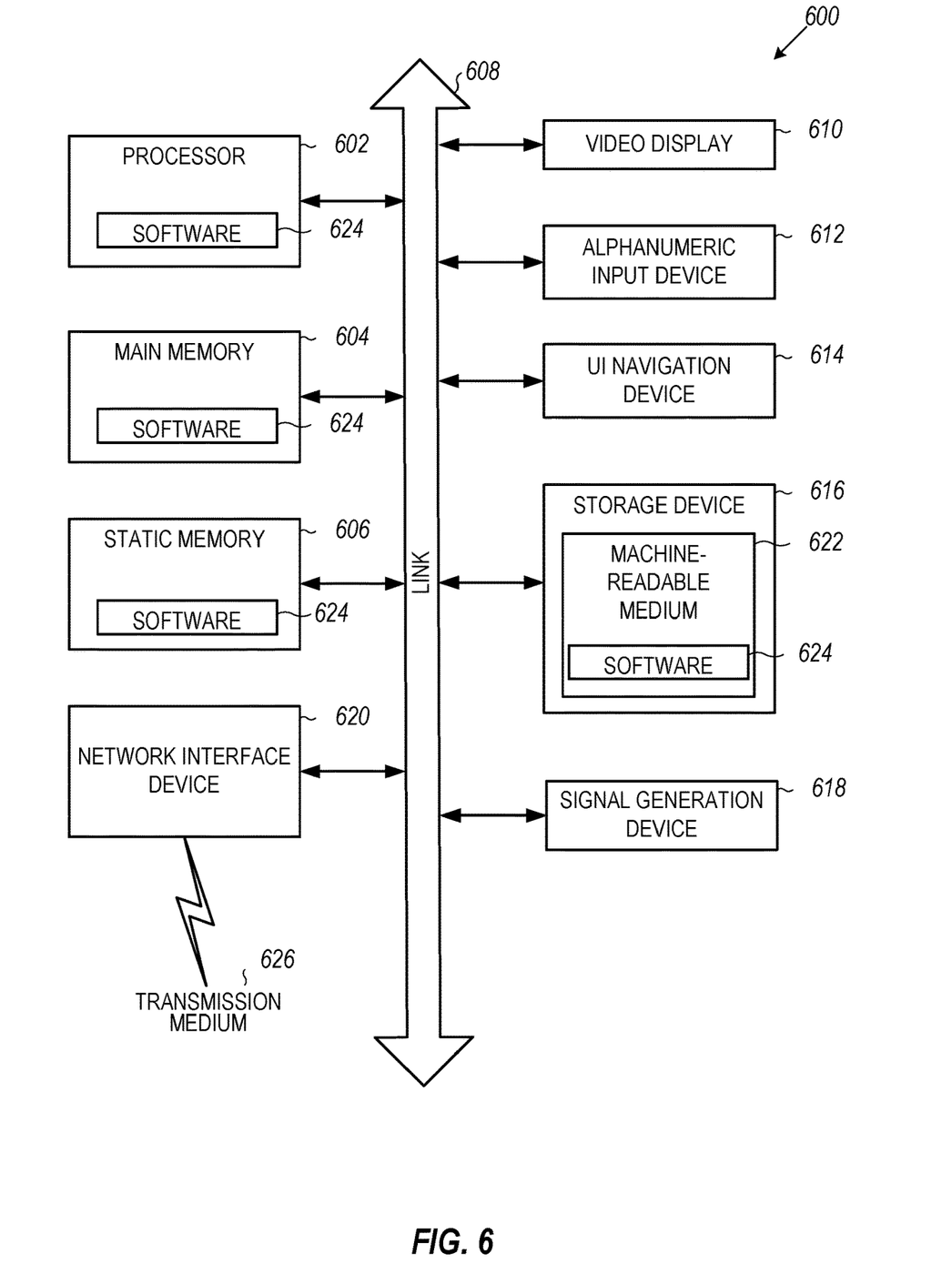
FIG. 6 is an example computing device that can be used in conjunction with the technologies described herein.

FIG. 6 is an example computing device that can be used in conjunction with the technologies described herein. In alternative embodiments, the computing device 600 may operate as a standalone device or may be connected (e.g., networked) to other computing devices. In a networked deployment, the computing device 600 may operate in the capacity of a server communication device, a client communication device, or both in server-client network environments. In an example, the computing device 600 may act as a peer computing device in peer-to-peer (P2P) (or other distributed) network environment. The computing device 600 may be a beacon reader, personal computer (PC), a tablet PC, a set top box (STB), a personal digital assistant (PDA), a mobile telephone, a smart phone, a web appliance, a network router, switch or bridge, or any computing device capable of executing instructions (sequential or otherwise) that specify actions to be taken by that computing device. Further, while only a single computing device is illustrated, the term "computing device" shall also be taken to include any collection of computing devices that individually or jointly execute a set (or multiple sets) of instructions to perform any one or more of the methodologies discussed herein, such as cloud computing, software as a service (SaaS), other computer cluster configurations. Computing device may be an implementation of a beacon reader 600, may implement components of the contact tracing system, and perform the method of FIG. 5.

Computing device 600 may include a hardware processor 602 (e.g., a central processing unit (CPU), a graphics processing unit (GPU), a hardware processor core, or any combination thereof), a main memory 604 and a static memory 606, some or all of which may communicate with each other via a link (e.g., bus) 608. The computing device 600 may further include a display unit 600, an input device 612 (e.g., a keyboard), and a user interface (UI) navigation device 614 (e.g., a mouse). In an example, the display unit 610, input device 612, and UI navigation device 614 may be a touch screen display. In an example, the input device 612 may include a touchscreen, a microphone, a camera (e.g., a panoramic or high-resolution camera), physical keyboard, trackball, or other input devices.

The computing device 600 may additionally include a storage device (e.g., drive unit) 616, a signal generation device 618 (e.g., a speaker, a projection device, or any other type of information output device), a network interface device 620, and one or more sensors, such as a global positioning system (GPS) sensor, compass, accelerometer, motion detector, or other sensor. The computing device 600 may include an input/output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.) via one or more input/output ports.

The storage device 616 may include a computing-readable (or machine-readable) storage media 622, on which is stored one or more sets of data structures or instructions 624 (e.g., software) embodying or utilized by any one or more of the techniques or functions described herein. In an example, at least a portion of the software may include an operating system and/or one or more applications (or apps) implementing one or more of the functionalities described herein. The instructions 624 may also reside, completely or at least partially, within the main memory 604, within the static memory 506, and/or within the hardware processor 602 during execution thereof by the computing device 600. In an example, one or any combination of the hardware processor 602, the main memory 604, the static memory 606, or the storage device 616 may constitute computing device (or machine) readable media.

While the computer-readable storage media 622 is illustrated as a single medium, a "computer-readable storage media" or "machine-readable storage media" may include a single medium or multiple media (e.g., a centralized or distributed database, and/or associated caches and servers) configured to store the one or more instructions 624.

In an example, a computer-readable storage media or machine-readable storage media may include any medium that is capable of storing, encoding, or carrying instructions for execution by the computing device 600 and that cause the computing device 600 to perform any one or more of the techniques of the present disclosure, or that is capable of storing, encoding or carrying data structures used by or associated with such instructions. Non-limiting computer-readable storage media examples may include solid-state memories, and optical and magnetic media. Specific examples of computer-readable storage media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); and optical media disks. The computer-readable storage media is non-transitory in that the storage media does not consist of transitory propagating signals.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. The network interface device 620 may use the transfer protocols to transmit data using transitory propagating signals.

In an example, the network interface device 620 may include one or more physical jacks (e.g., Ethernet, coaxial, or phone jacks) or one or more antennas to connect to the communications network 626. In an example, the network interface device 620 may include one or more wireless modems, such as a Bluetooth modem, a Wi-Fi modem or one or more modems or transceivers operating under any of the communication standards mentioned herein. In an example, the network interface device 620 may include a plurality of antennas to wirelessly communicate using at least one of single-input multiple-output (SIMO), multiple-input multiple-output (MIMO), or multiple-input single-output (MISO) techniques. In some examples, the network interface device 620 may wirelessly communicate using Multiple User MIMO techniques. In an example, a transmission medium may include any intangible medium that is capable of storing, encoding or carrying instructions for execution by the computing device 600, and includes digital or analog communications signals or like communication media to facilitate communication of such software.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

The above description is intended to be illustrative, and not restrictive. For example, the above-described examples (or one or more aspects thereof) may be used in combination with others. Other embodiments may be used, such as by one of ordinary skill in the art upon reviewing the above description. Further, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A method for contact tracing, the method comprising operations performed using an electronic processor, the operations comprising:
   receiving a first beacon identifier associated with a first person over a time period from a plurality of readers;
   receiving a second beacon identifier associated with a second person over the time period from the plurality of readers;
   determining first locations of the first person during the time period based on the received first beacon identifier;
   determining second locations of the second person during the time period based on the received second beacon identifier;
   receiving health data associated with the first person;
   determining, based on the health data, the first person is sick;
   determining, based on the health data, a sick period of time for the first person, wherein the sick period of time is within the time period;
   determining two or more people, including the second person, were within a proximity of the first person during the sick period based on the first locations, wherein the determining the second person was within the proximity of the first person during the sick period of period comprises determining the second person was within a predetermined distance from the first person; and
   generating a list of the two or more people that were within the proximity of the first person during the sick period.

2. The method of claim 1, wherein the determining the second person was within the proximity of the first person during the time period further comprises determining the second person was within the predetermined distance from the first person for more than a predetermined period of time.

3. The method of claim 1, further comprising removing, for the first person, access rights to a first location based on the determining the first person is sick.

4. The method of claim 3, further comprising adding, for the first person, access rights to a second location based on the determining the first person is sick.

5. The method of claim 1, further comprising determining, based on the first locations, possible infected locations the first person visited during the sick period of time.

6. The method of claim 5, further comprising removing access rights of a plurality of individuals to one of the possible infected locations.

7. The method of claim 5, further comprising:
   generating a cleaning schedule that includes each of the possible infected locations; and
   providing the cleaning schedule.

8. The method of claim 7, wherein providing the cleaning schedule comprises:
   determining a path to each of the possible infected locations; and
   altering video data to indicate the path.

9. The method of claim 5, further comprising altering video data to indicate one or more of the possible infected locations is closed.

10. The method of claim 1, further comprising altering video data to indicate the first person is sick.

11. The method of claim 1, wherein the receiving health data associated with the first person comprises receiving body temperature data of the first person from a camera.

12. The method of claim 1, wherein the health data comprises one or more of a temperature, heart rate, and oxygen amount.

13. The method of claim 1, wherein the receiving health data associated with the first person comprises receiving health data from a camera and a microphone.

14. The method of claim 13, further comprises:
   receiving audio data from a location associated with the first person; and
   generating the health data from the audio data.

15. The method of claim 14, wherein the generating the heath data from the audio data comprises detecting a cough from the audio data.

16. A system comprising:
   a non-transitory memory configured to store instructions executable by an electronic processor; and
   the electronic processor coupled to the non-transitory memory, wherein the electronic processor executes the instructions to:
      receive a first beacon identifier associated with a first person over a time period from a plurality of readers;
      receive a second beacon identifier associated with a second person over the time period from the plurality of readers;
      determine first locations of the first person during the time period based on the received first beacon identifier;
      determine second locations of the second person during the time period based on the received second beacon identifier;
      receive health data associated with the first person;
      determine, based on the health data, the first person is sick;
      determine, based on the health data, a sick period of time for the first person, wherein the sick period of time is within the time period;
      determine two or more people, including the second person, were within a proximity of the first person during the sick period based on the first locations, wherein to determine the second person was within the proximity of the first person during the sick period of period, the electronic processor is further configured to determine the second person was within a predetermined distance from the first person; and
      generate a list of the two or more people that were within the proximity of the first person during the sick period.

17. The system of claim 16, wherein to determine the second person was within the proximity of the first person during the time period, the electronic processor further executes instructions to determine the second person was within the predetermined distance from the first person for more than a predetermined period of time.

18. The system of claim 16, wherein the electronic processor further executes the instructions to:
   determine, based on the first locations, possible infected locations the first person visited during the sick period of time; and
   remove access rights of a plurality of individuals to one of the possible infected locations.

19. A non-transitory computer-readable storage medium storing computer-executable instructions, which, when executed by one or more processors, causes the one or more processors to:
- receive a first beacon identifier associated with a first person over a time period from a plurality of readers;
- receive a second beacon identifier associated with a second person over the time period from the plurality of readers;
- determine first locations of the first person during the time period based on the received first beacon identifier;
- determine second locations of the second person during the time period based on the received second beacon identifier;
- receive health data associated with the first person;
- determine, based on the health data, the first person is sick;
- determine, based on the health data, a sick period of time for the first person, wherein the sick period of time is within the time period;
- determine two or more people, including the second person, were within a proximity of the first person during the sick period based on the first locations, wherein causing the one or more processors to determine the second person was within the proximity of the first person during the sick period of period comprises causing the one or more processors to determine the second person was within a predetermined distance from the first person; and
- generate a list of the two or more people that were within the proximity of the first person during the sick period.

20. The non-transitory computer-readable storage medium of claim 19, wherein causing the one or more processors to determine the second person was within the proximity of the first person during the time period further comprises causing the one or more processors to determine the second person was within the predetermined distance from the first person for more than a predetermined period of time.

* * * * *